United States Patent [19]

Posey

[11] Patent Number: 4,707,906

[45] Date of Patent: Nov. 24, 1987

[54] METHOD OF ATTACHING TUBE TO A TUBE HOLDER

[76] Inventor: John T. Posey, 1739 Meadowbrook Rd., Altadena, Calif. 91001

[21] Appl. No.: 906,675

[22] Filed: Sep. 10, 1986

Related U.S. Application Data

[63] Continuation of Ser. No. 843,873, Mar. 25, 1986, abandoned, which is a continuation of Ser. No. 753,802, Jul. 3, 1985, abandoned, which is a continuation of Ser. No. 425,322, Sep. 28, 1982, abandoned.

[51] Int. Cl.$^4$ ............................................. B23P 11/02
[52] U.S. Cl. ........................................ 29/453; 24/339; 24/346; 24/72.5; 24/298; 248/74.2; 248/74.4
[58] Field of Search .................... 29/453, 450; 24/346, 24/335, 338, 339, 72.5; 248/74.2, 74.4

[56] References Cited

U.S. PATENT DOCUMENTS

| | | | |
|---|---|---|---|
| 556,209 | 3/1896 | Quinn | 24/338 X |
| 692,529 | 2/1902 | Knittle | 24/343 X |
| 803,464 | 10/1905 | Beck | 24/339 |
| 1,032,436 | 7/1912 | Smith | 24/331 X |
| 1,146,981 | 7/1915 | Weinberg | 24/335 X |
| 2,216,876 | 10/1940 | Crum | 248/74.2 |
| 2,400,058 | 5/1946 | Concannon | 24/338 X |
| 2,506,783 | 5/1950 | Fauteux, Jr. | 24/346 X |
| 2,651,826 | 9/1953 | Carpenter et al. | 24/339 X |
| 2,696,963 | 12/1954 | Shepherd | 24/339 X |
| 2,880,949 | 4/1959 | Fuss | 248/73 X |
| 2,961,479 | 11/1960 | Bertling | 248/74.2 X |
| 3,521,332 | 7/1970 | Kramer | 248/74.2 X |
| 3,599,916 | 8/1971 | Szabo | 24/339 X |
| 4,071,939 | 2/1978 | Bock | 29/453 X |
| 4,141,524 | 2/1979 | Corvese, Jr. | 248/74.2 X |
| 4,327,964 | 5/1982 | Haesly et al. | 29/453 UX |

FOREIGN PATENT DOCUMENTS 759867 10/1956 United Kingdom ................. 24/343

Primary Examiner—Charlie T. Moon
Attorney, Agent, or Firm—Christie, Parker & Hale

[57] ABSTRACT

A tube holder for hospital tubing comprises an elongated strip with opposing upper and lower faces formed as a plurality of side-by-side, open-ended sleeve like receptacles of varying enclosed cross-sectional area. In one embodiment, the strip is a spring metal piece with a reverse bend forming upper and lower legs with undulating surfaces formed in at least one of the legs, but preferably both of the legs, so that oppositely facing undulations on the upper and lower legs cooperate to form the spaced apart receptacles. Each receptacle has an entrance opening formed by a portion of the upper face being spaced from the lower face by a minimum distance. The entrance opening to each receptacle has a smaller dimension than the maximum dimension of its corresponding receptacle. Each receptacle is movable, say by prying apart the upper and lower legs to increase the spacing at the entrance openings for allowing tubing to slip sideways into any one of the receptacles. A releasable fastener, such as a spring loaded clip, is secured to an end of the strip for holding the tube holder in a fixed position on a bed, sheets, bedclothes, instruments or the like. Hospital tubing of a standard size can be slipped into the larger sized receptacle for confining the tubing but for allowing the tubing to move freely lengthwise through the receptacle. The same tubing can be inserted in the smaller sized receptacle which clamps onto opposite sides of the tubing for securely holding the tubing in place.

6 Claims, 4 Drawing Figures

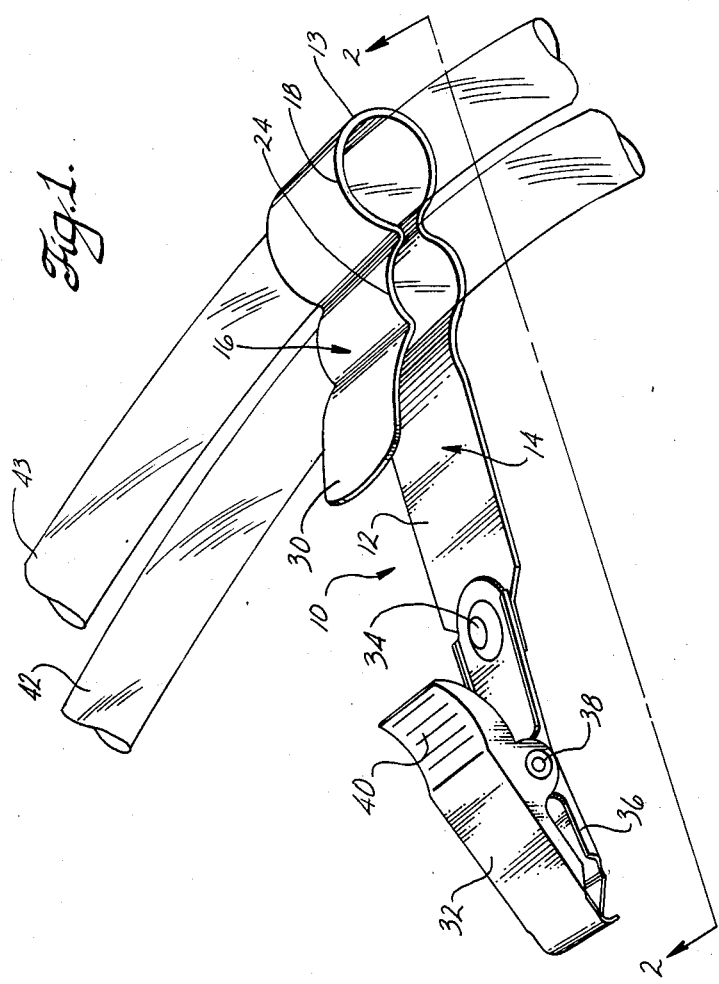

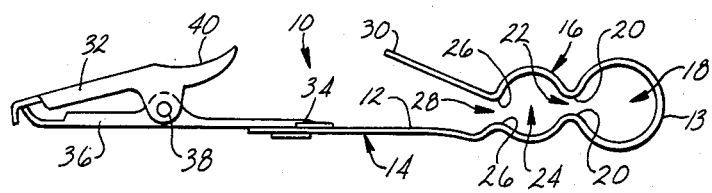
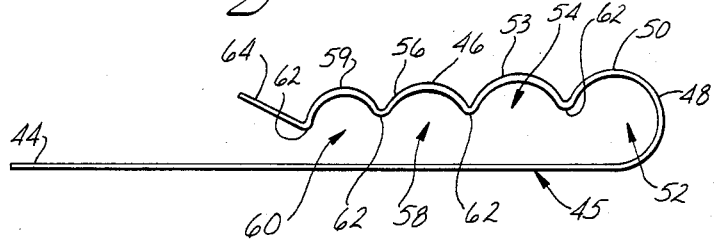
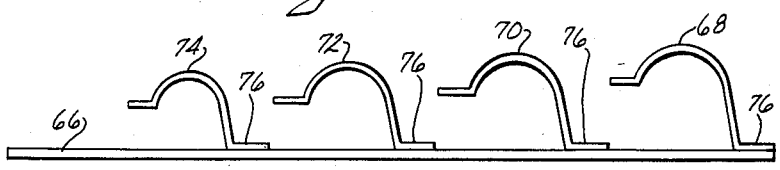

METHOD OF ATTACHING TUBE TO A TUBE HOLDER

CROSS REFERENCE TO RELATED APPLICATIONS

This application is a continuation application of Ser. No. 843,873 filed Mar. 25, 1986, now abandoned; which is a continuation application of Ser. No. 753,802 filed July 3, 1985, now abandoned; which is a continuation application of Ser. No. 425,322 filed Sept. 28, 1982, now abandoned.

FIELD OF THE INVENTION

This invention relates to a tube holder for attaching all forms of hospital tubing to sheets, beds, instruments, etc.

BACKGROUND OF THE INVENTION

Surgical tubing has many uses for patients confined to hospital beds. Drainage tubes and IV tubes are examples. Such tubing often creates a nuisance if left hanging loosely next to the patient's bed. It has been a common practice to use a safety pin for fastening the tubing to sheets, beds, or the patient's clothes to prevent the tubing from getting in the way. Sometimes there is a need to have hospital tubing confined (held out of the way) but still freely movable, and other times it is necessary to hold the tubing securely so it cannot move. A safety pin, for example, does not adequately serve these needs as a tube holder. In addition, safety pins, as well as other prior art tube holders, suffer from other disadvantages, such as a lack of convenience, being too cumbersome, and the inability to be sterilized and reused.

The present invention provides a tube holder that can hold surgical tubing securely, while it can just as easily hold the tubing in place but allow such tubing to be moved freely. The tube holder can adapt to surgical tubing of all standard sizes quickly and easily. Moreover, the tube holder can be sterilized or autoclaved.

SUMMARY OF THE INVENTION

Briefly, the tube holder of this invention comprises an elongated strip having a pair of opposed upper and lower faces forming at least a pair of spaced apart, open-ended, sleeve-like receptacles, each for confining a separate surgical tubing slipped into each receptacle. A clip is carried on an end portion of the strip opposite the receptacles. The clip releasably secures the tube holder to sheets, beds, instruments, bedclothes, or the like for confining tubing held in each receptacle. The receptacles are of different cross-sectional sizes so that a larger receptacle fits loosely around a tube that passes through it. This confines the tube but allows it to move freely lengthwise when desired. A smaller sized receptacle fits tightly around a tube of the same size to tightly secure the tube passing through the smaller sized receptacle. A number of receptacles of different sizes can be provided on the same tube holder.

In one embodiment, the tube holder is made from a single semi-rigid strip of material which is bent back on itself to form top and bottom legs which together are formed into side-by-side receptacles of different sizes. The two legs can be forced apart under a modest amount of tension to increase the spacing between them to facilitate slipping the tubing into one or more of the receptacles. The tension then can be simply released so the legs of the tube holder return to their normal positions for either loosely confining or tightly securing the tubing passing through the receptacles.

These and other aspects of the invention will be more fully understood by referring to the following detailed description and the accompanying drawings.

DRAWINGS

FIG. 1 is a perspective view illustrating a tube holder according to principles of this invention;

FIG. 2 is a side elevation view taken on line 2—2 of FIG. 1;

FIG. 3 is a fragmentary side elevation view showing an alterative embodiment of the tube holder; and FIG. 4 is a fragmentary side elevation view showing a further alternative embodiment of the tube holder.

DETAILED DESCRIPTION

FIGS. 1 and 2 illustrate one embodiment of a tube holder 10 according to principles of this invention. The main body of the tube holder is preferably made from a narrow, elongated, thin, flat, semi-rigid strip 12 of spring metal such as stainless steel. The strip 12 is bent back on itself with a reverse bend 13 to form a relatively longer lower leg 14 and a relatively shorter upper leg 16 which extends parallel to and is spaced above the lower leg 14. The portions of both legs which face each other are bent by the use of inside dies to form a pair of undulating surfaces which face each other to form a pair of longitudinally spaced apart open-ended, sleeve-like receptacles. The end of the strip having the reverse bend is formed with a rounded configuration to form a relatively larger receptacle 18 at the end of the tube holder. The upper and lower legs and the reverse bend are bent so that the wall of the larger receptacle is of circular curvature. As shown best in FIG. 2, the wall of the metal strip is bent with about 300° of wrap, terminating in a pair of oppositely facing ends 20 which are spaced apart at an entrance opening 22 to the larger receptacle 18.

The upper and lower legs of the metal strip are bent away from each other adjacent the entrance opening 22 to form opposite faces of a smaller receptacle 24 adjacent the larger receptacle 18. The upper and lower legs are bent so that each has a circular curvature and so the legs form curved upper and lower portions of the smaller receptacle. The curved portions of the upper and lower legs terminate in ends 26 closely spaced apart at an entrance opening 28 to the smaller receptacle. Thus, the smaller receptacle is formed by the curved portions of the upper and lower legs facing one another, leaving entrance openings 22 and 28 at opposite sides of the smaller receptacle, i.e., at the points where the spacing is the closest between the upper and lower legs.

The metal strip is bent so that the enclosed (circular) cross-sectional area within the larger receptacle is greater than the enclosed (circular) cross-sectional area within the smaller receptacle.

The upper leg of the strip terminates in a flanged end 30 which extends upwardly away from the entrance opening 28 to the smaller receptacle 24.

Thus, a pair of side-by-side open-ended tubular receptacles are formed, with the axes of the two receptacles being spaced apart longitudinally along the spring metal strip, and with the axes of the two receptacles being parallel to one another. The axes of the receptacles are also perpendicular to the length of the spring metal strip.

Although the illustrated embodiment shows a pair of receptacles, the spring metal strip also can be formed to provide a greater number of receptacles, each preferably having a progressively smaller enclosed cross-sectional area within it.

At the opposite end of the strip, a spring clip 32 is secured to the free end of the lower leg 14. The clip is conventional, having a flat base 36 attached to the strip by a rivet 34. The clip 32 is normally spring loaded to pivot about a pivot pin 38 so that the nose of the clip normally bears against the remote end of the base 36. The opposite end of the clip at 40 can be thumb-actuated to rotate the clip about the pin 38, against the bias of the torsion spring (not shown) wrapped around the pin, for opening the clip. Thus, the clip assists fastening the tubular holder to a fixture such as sheets, beds, instruments, etc. The attachment of the clip to the metal strip via the rivet 34 permits the clip to be rotated laterally through an angle in either direction about an axis through the rivet 34.

Use of the tube holder is best illustrated in FIG. 1. The receptacle portions of the tube holder are used for holding all forms of hospital tubing. The tubing is inserted into either of the receptacles, after which the tubing, restrained by the receptacles, is held in the fixed position by clipping the tube holder to any convenient fixture. In some instances, it is necessary to securely hold the tubing so that it cannot move. In this instance the tubing, such as the tubing 42 illustrated in FIG. 1, is placed in the smaller receptacle 24. Owing to the smaller cross-sectional area of the smaller receptacle, the opposite faces of the legs tightly clamp onto the tubing 42 and prevent it from moving lengthwise relative to the attached tube holder. In other instances, it is desirable to confine the tubing within the tube holder but to allow the tubing to freely move lengthwise relative to the tube holder. In this instance the tubing, such as the tubing 43 illustrated in FIG. 1, is placed in the larger receptacle 18. The larger receptacle is oversized slightly respect to the outside diameter of the tubing 43, thereby allowing the tubing to be moved freely lengthwise through the larger receptacle. The spacing at the entrance opening 22 to the larger receptacle is shorter than the outside diameter of the tubing so that the tubing is confined against lateral movement while retained inside the larger receptacle. It is preferred that the larger receptacle be at the end of the tube holder, bounded by the continuous end wall 13 at the reverse bend. This assists in confining an otherwise loosely fitting tube in the tube holder.

Thus, the tube holder illustrated in FIGS. 1 and 2 is adapted for use with a given standard size hospital tubing. The diameter of the larger receptacle is slightly greater than the outside diameter of the tubing, and the diameter of the circle defined by the smaller receptacle is slightly less than the diameter of the same tubing. The tube holder is made of spring metal so that when inserting the tubing in either receptacle some pressure is exerted on the flanged end 30 to pry apart the upper and lower legs of the tube holder. This, in effect, widens the entrance openings 28 and 22 to the smaller and larger receptacles so that the tubing can be slipped sideways into either receptacle, or both. By releasing the tension on the legs of the tube holder, the upper and lower legs of the tube holder, in their normal position, will confine the tubing in either receptacle. As for the tubing confined within the smaller receptacle, the spring bias of the opposite legs of the tube holder will apply a slight amount of tension to the opposite faces of the tubing for preventing the tubing from moving longitudinally within the smaller receptacle.

FIG. 3 illustrates an alternative form of the invention in which a tube holder is formed from a spring metal strip 44 having a flat lower leg 45 and an undulating upper leg 46. In the illustrated embodiment, there are four undulations in the upper leg of the spring metal strip, forming four side-by-side, open-ended sleeve-like receptacles of progressively smaller enclosed cross-sectional area. The metal strip has a reverse bend 48 with the largest undulation formed by a rounded upper surface 50 forming a first receptacle 52, a progressively smaller rounded upper surface 53 forming a progressively smaller second receptacle 54, a progressively smaller rounded upper surface 56 forming a third receptacle 58 which is smaller than the second receptacle 54, and a progressively smaller rounded upper surface 59 forming a fourth receptacle 60 which is the smallest of the four receptacles. The upper leg of the spring metal strip terminates in a flanged end 64. The separate rounded surfaces of the upper leg have ends 62 defining the points of minimum spacing between the upper and lower legs. These points are spaced apart along the length of the tube holder and define separate entrance openings to each receptacle. As with the tube holder 10, thumb pressure can be exerted on the flanged end 62 to pry apart the upper leg from the lower leg for increasing the width of the various entrance openings to the receptacle. This allows the hospital tubing to pass sideways into any of the receptacles. The tube holder of FIG. 3 is adapted for use with two different standard sizes of hospital tubing. The larger size tubing can be placed in either the first receptacle 52 or the second receptacle 54, depending upon whether the tubing is to be confined but freely movable or to be securely held in place. Similarly, a smaller standard size tubing can be placed in the third receptacle 58 if it is to be confined but freely movable, or it can be placed in the fourth receptacle 60 if it is to be securely held in place.

FIG. 4 illustrates a further alternative embodiment of the tube holder which comprises a flat spring metal strip 66 having four side-by-side open-ended receptacles formed by four retainers 68, 70, 72 and 74 of progressively smaller enclosed area. Each clip is a generally C-shaped spring metal piece and each has a flanged lower end 76 rigidly affixed to the strip 66, say by spot welding. The free end of each member has a minimum spacing from the lower leg of the tube holder, forming separate entrance openings to the receptacles formed by each member. The free end of each member can be pried away from the lower leg of the tube holder for slipping hospital tubing into any one of the receptacles.

Although the tube holder is preferably made of spring metal, the receptacle portion of the tube holder also can be made of hard, semi-rigid plastic. Preferably, a plastic with high temperature characteristics is used so the clip can be sterilized or autoclaved.

Thus, the tube holder of this invention fits various standard sizes of surgical tubing. It can hold a given piece of tubing in a fixed position preventing it from slipping, or it can confine the tubing but allow the tubing to freely move longitudinally. The tube holder is simple to apply, and it can be quickly attached to hospital sheets, beds, bedclothes, instruments and the like. In addition, the tube holder can be sterilized or autoclaved. The receptacle portion of the tube holder also can pivot relative to the clip to assist in securing the tube holder in any of a number of desired orientations.

What is claimed is:

1. A method for handling hospital tubing attached to a fixture used in a hospital, by selectively fixedly or slidably retaining the hospital tubing in a tube holder and affixed to the hospital fixture, the method comprising:

providing a tube holder in the form of an elongated support strip with a generally U-shaped reverse bend at one end forming opposite first and second legs on a tube-holding portion of the support strip, the tube holder having a pair of side-by-side resilient cylindrical receptacles formed by the first and second legs of the tube holder, each receptacle having an access opening expandable by flexure of the first and second legs for admitting the hospital tubing sideways into a selected one of the receptacles, each access opening being smaller than the diameter of the hospital tubing, one of the receptacles having a smaller diameter than the hospital tubing to fix the tubing to the holder by the applied tension of the first and second legs of the tube holder, the other of the receptacles having a slightly larger diameter than the same hospital tubing for slidably retaining the same tubing in the tube holder, the larger diameter receptacle being bounded by the reverse bend at the end of the tube holder so that the larger diameter receptacle slidably retains the hospital tubing while the reverse bend and the access opening to the larger diameter receptacle prevent sideways migration of the tubing in the larger receptacle, the tube holder further including a clip at an end opposite from the tube-holding portion of the tube holder for releasably attaching the tube holder to the hospital fixture; releasably attaching the clip to the hospital fixture; and flexing the legs of the tube holder and inserting the hospital tubing selectively in the smaller diameter receptacle to selectively fixedly retain the hospital tubing in the smaller diameter receptacle with the tension of the tube holder preventing longitudinal travel of the hospital tubing relative to the tube holder, or flexing the legs of the tube holder and moving the tubing farther into the tube holder by inserting the same hospital tubing into the larger diameter receptacle to selectively slidably retain the hospital tubing in the larger diameter receptacle at the end of the tube holder so the larger diameter receptacle normally resists sideways travel of the hospital tubing in the tube holder while permitting guided longitudinal travel of the hospital tubing relative to the tube holder.

2. The method according to claim 1 including retaining the hospital tubing in receptacles formed by undulating bends in at least one of the legs of the tube holder.

3. The method according to claim 2 including providing a flanged end adjacent the receptacle closest to the clip for use in prying apart the upper and lower legs of the tube holder.

4. The method according to claim 2 in which the first and second legs of the support strip have curved undulating bends facing one another for forming generally rounded sleeve-like receptacles.

5. The method according to claim 1 in which the receptacles are formed by a series of separate members of different sizes secured to and spaced apart along the length of the support strip.

6. The method according to claim 1 in which the tube holder is made from spring metal to permit autoclaving of the tube holder.

* * * * *